(12) United States Patent
Cho et al.

(10) Patent No.: US 9,351,924 B2
(45) Date of Patent: May 31, 2016

(54) DRUG DELIVERY SYSTEM INCLUDING LAMINATED STRUCTURE

(75) Inventors: Dong-Il Cho, Seoul (KR); Seok Jun Hong, Seoul (KR); Sang Min Lee, Seoul (KR); Jae Hyun Ahn, Seoul (KR); Hyoung Jung Yoo, Daegu (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/004,670

(22) PCT Filed: Sep. 20, 2011

(86) PCT No.: PCT/KR2011/006945
§ 371 (c)(1),
(2), (4) Date: Sep. 11, 2013

(87) PCT Pub. No.: WO2012/124869
PCT Pub. Date: Sep. 20, 2012

(65) Prior Publication Data
US 2014/0005600 A1    Jan. 2, 2014

(30) Foreign Application Priority Data

| Mar. 11, 2011 | (KR) | .................... | 10-2011-0021971 |
| Mar. 11, 2011 | (KR) | .................... | 10-2011-0021973 |
| Mar. 11, 2011 | (KR) | .................... | 10-2011-0021981 |
| May 16, 2011 | (KR) | .................... | 10-2011-0045826 |
| May 16, 2011 | (KR) | .................... | 10-2011-0045827 |
| May 16, 2011 | (KR) | .................... | 10-2011-0045828 |

(51) Int. Cl.
*A61K 9/00* (2006.01)
*A61M 37/00* (2006.01)
*A61K 9/24* (2006.01)
*A61K 9/28* (2006.01)
*A61K 9/70* (2006.01)

(52) U.S. Cl.
CPC .............. *A61K 9/0002* (2013.01); *A61K 9/209* (2013.01); *A61K 9/2853* (2013.01); *A61K 9/7007* (2013.01); *A61M 37/00* (2013.01)

(58) Field of Classification Search
CPC . A61K 9/0002; A61K 9/1635; A61K 9/1629; A61K 9/1647; A61K 9/209
USPC .............. 424/426, 422, 444, 93.4; 514/772.3
See application file for complete search history.

(56) References Cited

U.S. PATENT DOCUMENTS

| 3,916,899 | A | * | 11/1975 | Theeuwes ............... A61F 6/144 424/424 |
| 4,786,503 | A | | 11/1988 | Edgren et al. |
| 4,946,685 | A | | 8/1990 | Edgren et al. |
| 5,004,614 | A | * | 4/1991 | Staniforth ............ 424/466 |
| 6,126,956 | A | | 10/2000 | Grossman et al. |
| 6,638,536 | B2 | | 10/2003 | Savoir et al. |
| 7,241,457 | B2 | * | 7/2007 | Chen et al. ............ 424/468 |
| 2002/0052404 | A1 | * | 5/2002 | Hunter et al. ........... 514/449 |
| 2002/0128179 | A1 | * | 9/2002 | Tacon et al. ................ 514/2 |
| 2007/0061015 | A1 | * | 3/2007 | Jensen et al. .......... 623/23.51 |
| 2007/0128281 | A1 | * | 6/2007 | Patel .................... 424/473 |
| 2008/0268045 | A1 | * | 10/2008 | Dervieux et al. ......... 424/468 |
| 2009/0155326 | A1 | * | 6/2009 | Mack et al. ............... 424/402 |
| 2009/0263468 | A1 | * | 10/2009 | McAnulty et al. ......... 424/443 |
| 2009/0311190 | A1 | | 12/2009 | Gracias et al. |
| 2011/0104215 | A1 | | 5/2011 | Ito et al. |
| 2011/0104247 | A1 | | 5/2011 | Ito et al. |

FOREIGN PATENT DOCUMENTS

| JP | 2008-303151 A | 12/2008 |
| KR | 10-1995-0003918 B1 | 4/1995 |
| KR | 10-2002-0072290 A | 9/2002 |
| KR | 1020050081091 A | 8/2005 |
| KR | 10-2010-0037389 A | 4/2010 |
| KR | 10-2010-0126830 A | 12/2010 |
| WO | 95/15190 A1 | 6/1995 |
| WO | 2009/032655 A1 | 3/2009 |

OTHER PUBLICATIONS

Ratner et al. (Biomedical Engineering Desk Reference, Published 2009, pp. 215-217).*
International Search Report issued in PCT/KR2011/006945 with Date of mailing Apr. 4, 2012.

* cited by examiner

*Primary Examiner* — Alma Pipic
(74) *Attorney, Agent, or Firm* — McDermott Will & Emery LLP

(57) ABSTRACT

One aspect of the present invention relates to a drug delivery system comprising a layered structure where a drug layer and a biodegradable polymer layer for controlling the release of drugs are alternately laminated. The drug delivery system can easily control an in-vivo drug release rate and a release amount.

10 Claims, 1 Drawing Sheet

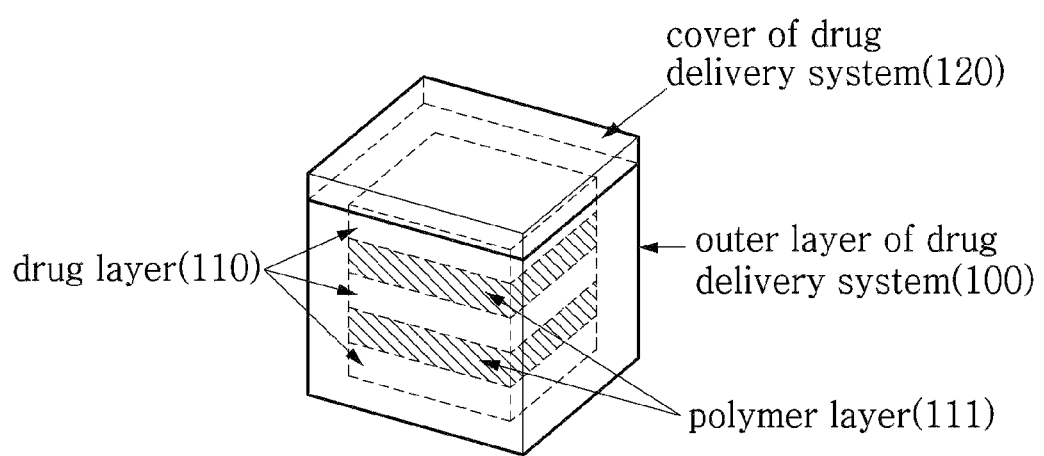

DRUG DELIVERY SYSTEM INCLUDING LAMINATED STRUCTURE

RELATED APPLICATIONS

This application is the U.S. National Phase under 35 U.S.C. §371 of International Application No. PCT/KR2011/006945, filed on Sep. 20, 2011, which in turn claims the benefit of Korean Patent Application No. 10-2011-0021971, filed on Mar. 11, 2011, Korean Patent Application No. 10-2011-0021973, filed Mar. 11, 2011, Korean Patent Application No. 10-2011-0021981, filed Mar. 11, 2011, Korean Patent Application No. 10-2011-0045826, filed May 16, 2011, Korean Patent Application No. 10-2011-0045827, filed May 16, 2011, and Korean Patent Application No. 10-2011-0045828, filed May 16, 2011, the disclosures of which are incorporated by reference herein.

BACKGROUND

1. Field

The present disclosure relates to a drug delivery system comprising a layered structure.

2. Description of the Related Art

In order for a drug to act effectively in a living area, the drug must be able to be expressed in the intended target area, and the in vivo concentration of the drug in the target area should be maintained in the therapeutic range for a certain period of time or longer. If a drug is present in an excessive amount in the body, it will show toxicity, and if the drug is present in an exceedingly small amount, it will show no therapeutic effect. A drug delivery system can function to control the amount of a drug in the body.

SUMMARY

In accordance with an aspect of the present disclosure to provide a drug delivery system, which can gradually release the drug to maintain the concentration of the drug in a target area at a high level and makes it possible to easily control the rate or amount of release of the drug.

An aspect of the present disclosure provides a drug delivery system comprising a layered structure in which a drug layer and a biodegradable polymer layer for drug release control are alternately stacked.

The drug delivery system according to the present disclosure comprises a layered structure in which a drug layer and a biodegradable polymer layer for drug release control are alternately stacked. Thus, the drug delivery system of the present disclosure can gradually release the drug to maintain the concentration of the drug in a target area at a suitable level and makes it possible to easily control the rate or amount of release of the drug.

BRIEF DESCRIPTION OF THE DRAWINGS

FIG. 1 shows an example of a drug delivery system comprising a layered structure according to an aspect of the present disclosure.

DETAILED DESCRIPTION

As used herein, the term "drug delivery system" refers to a drug formulation designed to control the release rate of the drug or efficiently deliver the drug to a target area.

As used herein, the term "polymer" refers to a compound having a molecular weight of 10,000 or higher, and the term "biodegradable" refers to the property of being degradable in vivo.

A biodegradable polymer drug delivery system can deliver the drug into a specific selected area in a simple manner, and a separate surgical operation for removing the drug delivery system is not required. Due to these advantages, the drug delivery system is highly useful in the clinical medical field and has been extensively studied in various fields, including pharmacology, polymer chemistry and biotechnology.

A conventional biodegradable polymer drug delivery system is generally made of one kind of biodegradable polymer and has a simple shape. For this reason, it cannot have special functions other than a simple function of releasing the drug following biodegradation, and it is difficult for the drug delivery system to maintain the concentration of the drug in and around a target area at a high level. Thus, the conventional drug delivery system cannot be widely used in the clinical medical field.

Hereinafter, the present disclosure will be described in detail.

An aspect of the present disclosure provides a drug delivery system comprising a layered structure in which a drug layer and a biodegradable polymer layer for drug release control are alternately deposited. When this drug delivery system is administered in vivo, the biodegradable polymer layer for drug release control will be degraded so that the drug in the underlying drug layer can be released. Thus, the rate or amount of release of the drug can be controlled depending on the thickness or area of the biodegradable polymer layer for drug release control or the kind of polymer. Accordingly, the drug delivery system according to an aspect of the present disclosure can accurately control the rate or amount of release of the drug compared to a conventional drug delivery system, and thus can control the amount of release of the drug in a target area to maintain the concentration of the drug in the target area at a high level. In addition, when the drug layers contain different drugs, the different drugs can be released from the drug delivery system over time after administration in vivo. This will be particularly useful when the different drugs need to be released in different areas during the in vivo movement of the drug delivery system.

The layered structure of the drug delivery system according to an aspect of the present disclosure can vary depending on the number of the drugs to be released or the areas in which the drugs are to be released. In another aspect of the present disclosure, the layered structure may comprise 2-10 layers, and preferably 4-8 layers. In this case, the number of the stacked drug layers may be the same as or different from the number of the biodegradable polymer layers for drug release control.

The drug delivery system according to an aspect of the present disclosure may comprise a plurality of biodegradable polymer layers for drug release control, and the polymers of the polymer layers may have different biodegradation rates. Using the polymers of the polymer layers, which have different biodegradation rates, the rate or amount of release of the drug from the drug layers stacked alternately with the polymer layers can be controlled in an easy and accurate manner. The drug delivery system according to another aspect of the present disclosure may have 2-5 biodegradable polymer layers, and preferably 2-4 biodegradable polymer layers. In still another aspect of the present disclosure, the biodegradable polymer may include one or more selected from the group consisting of poly-caprolactone (PCL), L-poly-lactide (LPLA), poly-glycolic acid (PGA), poly-D-lactide (PDLA), poly-lactic acid (PLA), poly-lactic-co-glycolic acid (PLGA), polyvinylacetate phthalate, a methacrylic acid polymer, and hydroxypropyl methylcellulose phthalate, but is not limited thereto.

The drug layer of the drug delivery system according to an aspect of the present disclosure may be a layer made only of a drug. In another aspect of the present disclosure, the drug layer may be a drug layer comprising a biodegradable polymer, that is, a layer that is prepared based on a biodegradable polymer and comprises a drug.

The drug delivery system according to an aspect of the present disclosure may further comprise a biodegradable polymer outer layer surrounding the layered structure. This drug delivery system can control the time point, rate or amount of release of the drug by controlling the biodegradation rate of the polymer of the outer layer.

In another aspect of the present disclosure, the polymer outer layer may have a thickness of 10-30 μm, and preferably 15-20 μm. When the polymer outer layer has a thickness in the above range, it can show the effect intended in the present disclosure, can satisfy both the stability and safety of the drug delivery system and can be suitable in terms of the cost versus effect.

In an aspect of the present disclosure, the polymer outer layer may comprise an opening. In this case, in order to establish the order in which the drugs of the drug layers are released, that is, in order for the drug of the drug layer close to the opening to be preferentially released, the polymer of the polymer outer layer may have a biodegradation rate than those of the polymers of the polymer layers of the layered structure.

In an aspect of the present disclosure, the drug delivery system may further comprise a polymer cover covering the opening, and in this case, the biodegradation rate of the polymer may be lower in the order of the layer of the outer layer, the polymer of the polymer layers of the layered structure, and the polymer of the cover. The cover serves to determine the time point of release of the drug from the drug delivery system, and the time point of release of the drug can be determined by controlling the thickness and area of the cover or the kind of cover polymer. In another aspect of the present disclosure, the polymer of the polymer outer layer may include poly-caprolactone (PCL) or L-poly-lactide (LPLA); the polymer of the biodegradable polymer layers for drug release control may include poly-glycolic acid (PGA) or poly-D-lactide (PDLA); and the polymer of the polymer cover may include poly-lactic acid (PLA) or poly-lactic-co-glycolic acid (PLGA).

In an aspect of the present disclosure, an area in which the drug is released or the release rate of the drug can be controlled by controlling the area and thickness of the outer layer, the biodegradable polymer layers for drug release control in the layered structure, or the polymer cover. In another aspect of the present disclosure, the polymer outer layer may have a thickness of 10-30 μm, and preferably 15-20 μm, the biodegradable polymer layers for drug release control in the layered structure may have an area of 400-10,000 μm$^2$, and preferably 4,000-6,000 μm$^2$, and the polymer cover may have an area of 5,000-12,000 μm$^2$, and preferably 6,000-8,000 μm$^2$. The thickness or area in the above ranges can show the effect intended in the present disclosure, can satisfy both the stability and safety of the drug delivery system and can be suitable in terms of the cost versus effect.

FIG. 1 shows an example of a drug delivery system according to an aspect of the present disclosure, which comprises an outer layer 100 of the drug delivery system, a drug layer 110, a biodegradable polymer layer 111 for drug release control, and a cover 120 of the drug delivery system. The drug delivery system shown in FIG. 1 is illustrative only, but the scope of the present disclosure is not limited thereto.

The drug delivery system according to an aspect of the present disclosure may comprise two or more drug layers, in which the drug layers may comprise the same or different drugs. In another aspect of the present disclosure, the drug may include any substance that can be applied to animals, including humans, or plants, in order to treat or prevent diseases or wounds. In addition, the drug is also meant to include general therapeutic drugs, enzymes, or biochemical substances such as miRNA. In another aspect of the present disclosure, the drug may be liquid or solid. In another aspect of the present disclosure, the drug may include one or more selected from among non-steroidal anti-inflammatory drugs, calcium channel blockers, angiotensin II antagonists, hyperlipidemia treating drugs, diabetes treating drugs, lipase inhibitors, antihistamine drugs, drugs for treating diseases of the digestive system, platelet aggregation inhibitors, osteoporosis treating drugs, antiviral drugs, antibiotics, antifungal drugs, immunosuppresants, hormone drugs, antitumor drugs, salts thereof and pharmaceutical derivatives thereof. In still another aspect of the present disclosure, the drug may be one or more selected from among non-steroidal anti-inflammatory drugs, including acetaminophen, acetylsalicylic acid, ibuprofen, flurbiprofen, indometacin, naproxen, ketoprofen, piroxicam or aceclofenac; calcium channel blockers, including nifedipine or nimodipine: angiotensin H antagonists, including valsartan, irbesartan, candesartan, olmesartan or losartan; hyperlipidemia treating drugs, including atorvastatin, lovastatin, simvastatin, fluvastatin, gemfibrozil or fenofibrate; diabetes treating drugs, including rosiglitazone or metformin; lipase inhibitors, including orlistat; antihistamine drugs, including phenylamine or fexofenadine; drugs for treating diseases of the digestive system, including omeprazole, pantoprazole, famotidine or cimetidine; platelet aggregation inhibitors, including cilostazol or clopidogrel; osteoporosis treating drugs, including raloxifene; antiviral drugs, including acyclovir, famciclovir or lamivudine; antibiotics, including clarithromycin, ciprofloxacin or cefuroxime; antifungal drugs, including itraconazole, amphotericin B, terbinafine, fluconazole or ketoconazole; immunosuppresants, including cyclosporine, tacrolimus or rapamycin; hormone drugs, including testosterone, prednisolone, estrogen, cortisone, hydrocortisone or dexamethasone; antitumor drugs, including paclitaxel, docetaxel, doxorubicin or busulfan; salts thereof; and pharmaceutical derivatives thereof, but is not limited thereto.

The drug delivery system according to an aspect of the present disclosure may have a spherical shape. The drug delivery system according to another aspect of the present disclosure may have a polyhedral shape, in which examples of the polygonal shape include, but are not limited to, tetrahedral to decahedral shapes, preferably tetrahedral to octahedral shapes, and more preferably tetrahedral to hexahedral shapes. Conventional drug delivery systems mostly have a spherical shape in order to linearly maintain drug release following biodegradation. When such spherical biodegradable polymer drug delivery systems are surface-treated in order to impart various functions, it is not easy, due to the characteristics of the sphere, to divide the surface into several regions and surface-treat only a specific region among the divided regions. For this reason, in this case, it is difficult to impart various functions to the drug delivery systems. However, the drug delivery system according to an aspect of the present disclosure has a polyhedral shape, and thus it is possible to accurately divide the surface of the micro-sized drug delivery system into several regions and surface-treat only a specific desired region among the divided regions, unlike the case of the conventional drug delivery systems. In still another aspect of the present disclosure, when the polyhedral shape is more preferably a hexahedral shape, because it is particularly easy to divide the outer surface into several regions and surface-treat only a specific region among the divided regions.

The drug delivery system according to an aspect of the present disclosure may comprise one or more treated outer surfaces for imparting functions to the drug delivery system. The drug delivery system according to another aspect of the present disclosure may comprise two or more treated outer surfaces, in which the treated outer surfaces may be those surface-treated in different manners. In still another aspect of the present disclosure, only a portion of the surface-treated surface region may be surface-treated.

In an aspect of the present disclosure, the surface treatment may be performed by one or more of physical etching, chemical etching, coating with a chemical material, and adsorption of microorganisms. Herein, the chemical material may be, for example, bovine serum albumin (BSA). The drug delivery system according to the present disclosure can be effectively surface-treated by a surface treatment process having straightness, such as plasma treatment or chemical vapor deposition.

In an aspect of the present disclosure, the microorganisms include microorganisms having mobility with flagella. Specifically, the microorganisms include microorganisms having mobility (i.e., taxis) which is directed in response to external stimulus. More specifically, the microorganisms include microorganisms having taxis for cancer cells. When the drug delivery system is surface-treated by adsorption of microorganisms as described above, the adsorbed microorganisms will move in response to a specific environment or a disease such as cancer, and thus the drug delivery system will move to a target area. In another aspect of the present disclosure, the microorganisms may be microorganisms that can self-replicate so as to sufficient mobility to the drug delivery system until the drug delivery system reaches a target area. In still another aspect of the present disclosure, in the case in which microorganisms are adsorbed onto the outer surface of the drug delivery system comprising the polymer outer layer having low biodegradation rate, the drug delivery system can still retain the ability to move by the adsorbed microorganisms, even when the drug is released through the opening.

In still another aspect of the present disclosure, the microorganisms include, but are not limited to, bacteria, including *Escherichia coli*, *Serratia marcescens* and *Salmonella typhimurium*.

An aspect of the present disclosure provides a method for preparing a drug delivery system, comprising alternately stacking a drug layer and a biodegradable polymer layer for drug release control. Alternately stacking the drug layer and the biodegradable polymer layer for drug release control may comprise alternately injecting a drug and a polymer. Another aspect of the present disclosure provides a method for preparing a drug delivery system comprising a polymer outer layer, the method comprising: preparing a polymer outer layer; and alternately stacking a drug layer and a biodegradable polymer layer for drug release control. Still another aspect of the present disclosure provides a method for preparing a drug delivery system comprising a polymer cover, the method comprising: preparing a polymer outer layer; alternately stacking a drug layer and a biodegradable polymer layer for drug release control; and forming a polymer cover covering an opening. Covering the polymer cover may comprise injecting a polymer into the opening of the outer layer by a micro syringe.

Although the preferred embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. A drug delivery system comprising a layered structure in which at least two drug layers and at least one biodegradable polymer layer for drug release control are alternately stacked; and
   a biodegradable polymer outer layer surrounding the layered structure,
   wherein the biodegradable polymer outer layer comprises an opening,
   wherein the drug delivery system further comprises a polymer cover covering the opening,
   wherein the biodegradable polymer outer layer, the at least one biodegradable polymer layer for drug release control and the polymer cover each have a different biodegradation rate, and
   wherein the biodegradation rate of the biodegradable polymer outer layer is lower than the biodegradation rate of the at least one biodegradable polymer layer for drug release control, and the biodegradation rate of the at least one biodegradable polymer layer for drug release control is lower than the biodegradation rate for the polymer cover,
   wherein one of the at least one biodegradable polymer layer is between each of the at least two drug layers, and
   wherein the size of the opening encompasses the entire outer surface of the at least one drug layer located proximal to the opening.

2. The drug delivery system of claim 1, wherein the layered structure comprises 3-10 layers.

3. The drug delivery system of claim 1, wherein the layered structure has a plurality of the at least one biodegradable polymer layer for drug release control, and polymers of the plurality of at least one biodegradable polymer layer have different biodegradation rates.

4. The drug delivery system of claim 1, wherein the biodegradable polymer outer layer comprises poly-caprolactone (PCL) or L-poly-lactide (LPLA), the at least one biodegradable polymer layer for drug release control comprises poly-glycolic acid (PGA) or poly-D-lactide (PDLA), and the polymer cover includes poly-lactic acid (PLA) or poly-lactic-co-glycolic acid (PLGA).

5. The drug delivery system of claim 1, which has any one shape of tetrahedral to decahedral shapes.

6. The drug delivery system of claim 5, which comprises one or more outer surfaces subjected to surface treatment.

7. The drug delivery system of claim 6, wherein the surface treatment is performed by one or more of physical etching, chemical etching, coating with a chemical material, and adsorption of microorganisms.

8. The drug delivery system of claim 7, wherein the microorganisms include one or more selected from the group consisting of *Escherichia coli*, *Serratia marcescens* and *Salmonella typhimurium*.

9. The drug delivery system of claim 7, wherein the surface treatment is performed by the adsorption of microorganisms, and the adsorbed microorganisms provide mobility to the drug delivery system to a target area in response to a specific environment.

10. The drug delivery system of claim 1, wherein the at least two drug layers each contain a different drug.

\* \* \* \* \*